(12) United States Patent
Raa et al.

(10) Patent No.: US 12,337,011 B2
(45) Date of Patent: Jun. 24, 2025

(54) DECONSTRUCTED SOIL

(71) Applicant: Ederagen AS, Oslo (NO)

(72) Inventors: Jan Raa, Oslo (NO); Pål Trosvik, Oslo (NO); Eric De Muinck, Nesøya (NO)

(73) Assignee: Ederagen AS, Oslo (NO)

( * ) Notice: Subject to any disclaimer, the term of this patent is extended or adjusted under 35 U.S.C. 154(b) by 848 days.

(21) Appl. No.: 17/621,755

(22) PCT Filed: Jun. 25, 2020

(86) PCT No.: PCT/EP2020/067901
§ 371 (c)(1),
(2) Date: Dec. 22, 2021

(87) PCT Pub. No.: WO2020/260498
PCT Pub. Date: Dec. 30, 2020

(65) Prior Publication Data
US 2022/0354881 A1    Nov. 10, 2022

(30) Foreign Application Priority Data
Jun. 28, 2019    (NO) .................................. 20190820

(51) Int. Cl.
| | | |
|---|---|---|
| *A61K 31/716* | (2006.01) | |
| *A61K 31/717* | (2006.01) | |
| *A61K 33/06* | (2006.01) | |
| *A61K 33/26* | (2006.01) | |
| *A61K 36/064* | (2006.01) | |

(52) U.S. Cl.
CPC .......... *A61K 31/716* (2013.01); *A61K 31/717* (2013.01); *A61K 33/06* (2013.01); *A61K 33/26* (2013.01); *A61K 36/064* (2013.01)

(58) Field of Classification Search
None
See application file for complete search history.

(56) References Cited

U.S. PATENT DOCUMENTS

| | | |
|---|---|---|
| 5,032,401 A | 7/1991 | Jamas et al. |
| 2004/0131705 A1 | 7/2004 | Lown et al. |

FOREIGN PATENT DOCUMENTS

| | | |
|---|---|---|
| CN | 108946961 A | 12/2018 |
| DE | 102014104335 A1 | 10/2015 |
| JP | 2005154398 A | 6/2005 |
| WO | 2011007320 A1 | 1/2011 |

OTHER PUBLICATIONS

Cole, J. et al.; "Ribosomal Database Project: data and tools for high throughput rRNA analysis"; Nucleic Acids Research, vol. 42, Database Issue; 2014; pp. D633-D642.
De Muinck, E., et al.; "A novel ultra high-throughput 16S rRNA gene amplicon sequencing library preparation method for the Illumina HiSeq platform"; Microbiome, vol. 5, Issue No. 68; 2017; 15 pages; doi: 10.1186/s40168-017-0279-1.
International Search Report and Written Opinion for International Application PCT/EP2020/067901; International Filing Date: Jun. 25, 2020; Date of Mailing: Oct. 5, 2020; 12 pages.
Swidsinski, A. et al.; "Impact of Humic Acids on the colonic microbiome in healthy volunteers"; World Journal of Gastroenterology, vol. 23, Issue No. 5; 2017; p. 885-890.
Altschul, S. et al.; "Basic Local Alignment Search Tool"; Journal of Molecular Biology, vol. 215; 1990; pp. 403-440.
Hamza, Z. et al.; "Preparation and characterization of yeast cell wall beta-glucan encapsulated humic acid nanoparticles as an enhanced aflatoxin B1 binder"; Carbohydrate Polymers, vol. 203; 2019; pp. 185-192.
Vetvicka, V. et al.; "Glucan and Humic Acid: Synergistic Effects on the Immune System"; Journal of Medicinal Food, vol. 13, Issue No. 4; 2010; pp. 863-869.
Vetvicka, V. et al.; "Synergistic Effects of Humic Acid and Glucan in Hepatoprotection against Experimental Liver Injury"; Austin Journal of Clinical Pathology, vol. 1, Issue No. 4; 2014; 4 pages.
Suzuki, T. et al. Research and Development of beta-1,3-1,6-Glucan from Black Yeast for a Functional Food Ingredient, Journal of Applied Glycoscience, vol. 2, No. 1, p. 51-60 (2012). With Partial Translation.

*Primary Examiner* — Brian Gangle
(74) *Attorney, Agent, or Firm* — Karen A. LeCuyer; DeWitt LLP

(57) ABSTRACT

The invention comprises a defined and safe soil substitute, herein referred to as "deconstructed soil", that supports ecological balance in anaerobic microbial ecosystems, such as that inside the human gut, by shifting energy availability to favor growth of bacteria linked with gut health, and away from the most dominant species and species that are putatively harmful. The invention enables vulnerable bacterial groups to recover from a state of apparent extinction from the ecosystem in question. As it does not contain components that are prebiotic or probiotic, the deconstructed soil represents a new product concept for preventing and treating conditions associated with dysfunctional microbial ecosystems in the gastrointestinal tract of humans and animals, as well as other anaerobic microbial ecosystems.

16 Claims, 15 Drawing Sheets

DECONSTRUCTED SOIL

CROSS REFERENCE TO RELATED APPLICATIONS

Figure 1:
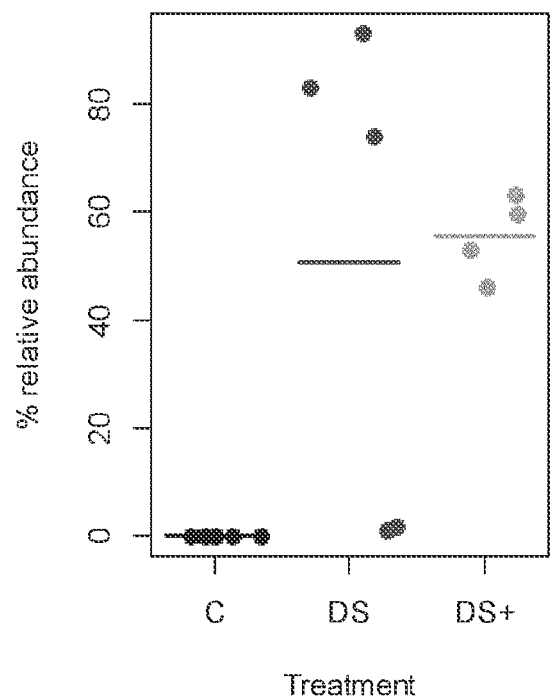

This application is a National Stage application of PCT/EP2020/067901, filed Jun. 25, 2020, which claims priority to Norwegian Patent Application No. 20190820, filed Jun. 28, 2019, both of which are incorporated by reference in their entirety herein.

FIELD OF THE INVENTION

The present invention relates to a deconstructed soil (DS) composition and use thereof in modulating microbial ecosystems by facilitating recovery of vulnerable bacterial species in the gut microbiota and favouring beneficial bacterial groups at the expense of species with putative negative health effects.

BACKGROUND OF THE INVENTION

The epidemic nature of western lifestyle diseases is most likely the result of modern living conditions deviating too much from the natural environments to which the human species has become adapted throughout biological evolution. Highly processed foods, aseptic environments, misunderstood hygiene practices and lack of exposure to soil and other products in natural environments may all be contributing factors. Such lifestyle diseases are associated with ecological disturbances in the community of gut microorganisms, the so-called gut microbiota (GM). These ecological disturbances, often referred to as GM dysbiosis, have been linked with a variety of disease conditions which represent a fundamental departure from the "one microbe—one disease" concept that has dominated medical science for generations. Attempts to prevent or heal diseases associated with GM dysbiosis, must therefore be based on understanding of how extremely complex ecosystems such as GMs function and respond to food and other environmental inputs. The relevance of the deconstructed soil described herein is that it modulates the GM according to basic ecological principles and may therefore be a preferred product category for counteracting lifestyle diseases in the urbanized western world.

The Biological Rationale of Geophagy

The DS concept as described herein may be better understood and appreciated when brought into a wider biological and evolutionary context. Voluntary ingestion of soil, called geophagy, is widespread among animals and in human populations. In humans, the practice is particularly common among children as well as pregnant women in many cultures. The biological rationale behind this behaviour is not fully understood. But since it is so widespread, it can be assumed that it contributes with something beneficial. If dangerous or deleterious, geophagy would have been discarded by evolution.

Soil is a source of minerals. Voluntary ingestion of soil is therefore often seen as an instinctive way of securing adequate supply of minerals and micro-nutrients. Although geophagy is a normal human behavior, it is regarded as disgusting, odd and perverted by most people in western societies. There is accordingly no social or mental acceptance of geophagy as a health promoting practice, and it is not appreciated by medical professionals. Even if it were accepted, it would not be recommendable in the modern era due to the risks associated with contamination by heavy metals, toxic chemicals and potential pathogens, in particular in urbanized regions.

It has been shown that soil exposure significantly modulates the GM of mice, and it has been shown in model experiments that mice raised on a soil containing bedding, were less prone to asthma. Furthermore, repeated skin exposure to a soil preparation has been associated with an elevated microbial diversity in the GM of healthy humans. High exposure to non-polluted soil and components present in natural environments is also thought to contribute to reduced incidence of non-communicative diseases in rural populations and hunter-gatherer tribes. These effects are generally ascribed to exposure to live microbes in these environments, while little attention has been paid to the abiotic components of soil, such as those in the DS presented herein. The DS product of the present invention represents a sterile, safe and consistent substitute to natural soil exposure.

PRIOR ART

In contrast to existing products addressing GM dysbiosis, the DS described herein contains no live microbes (probiotics), no energy substrates for microbes (prebiotics), and no metabolites left behind in growth media in which microbes have been cultivated (postbiotics). The invention considers the ecological complexity inherent in GM ecosystems by promoting energy distribution between community members instead of introducing live bacteria or supplying extra energy to specific groups of microbes in this community.

Probiotics aim to introduce large numbers of one or a few bacterial species into the GM. Probiotic bacteria, mostly lactic acid bacteria and often alien to the human gut, are usually regarded as beneficial. There is, however, little scientific support for this notion. In the case of *Lactobacillus* sp., the most common bacteria used in probiotic preparations, an individual will normally harbor resident species and strains that are already adapted to the host environment, and these normally occur at relatively low abundances in the human colon.

Microbiomes are highly individual, and the isolation of probiotic strains from diverse sources may not be an appropriate approach for introducing putatively beneficial microbes into hosts with differing GM ecologies. This is important because many of the health effects claimed for probiotics are strain specific. Unlike probiotics, the invention presented here does not introduce any live microbes but helps to provide suitable conditions for the resident bacteria to exist in the host to which they are adapted, and to co-exist with other microorganisms in the same ecosystem.

Prebiotics as a concept was defined in 1995 and has since undergone many changes to its definition. According to the International Scientific Association for Probiotics and Prebiotics (ISAPP) a prebiotic is "a substrate that is selectively utilized by host microorganisms conferring a health benefit". The term 'substrate' means a substance on or from which an organism obtains its nourishment. Most prebiotics are oligosaccharides which are growth substrates for putative beneficial bacteria, primarily lactic acid bacteria and bifidobacteria.

The DS of the present invention does not contain any energy substrates for growth of bacteria under anaerobic conditions, and its effects on GM-ecology described in the examples below, must therefore be due to other mechanisms.

Postbiotics are low molecular weight microbial metabolites, including quorum sensing molecules, produced during microbial growth and left behind in cultivation media. There are no such metabolites in the product of this invention.

An alternative to the use of pro-, pre- and postbiotics to modulate the GM is to transplant complete microbial ecosystems in the form of fresh feces from healthy donors, so-called Fecal Microbiota Transplantation (FMT). FMT has been very successful in the treatment of antibiotics associated diarrhea caused by *Clostridium difficile*. This is a bacterium normally present in healthy GMs, but in extreme cases of GM-dysbiosis, most often caused by antibiotics, it becomes a life-threatening toxin producer. FMT is, however, not a realistic alternative for treatment of lifestyle diseases caused by dysbiotic GM and it is a method outside the scope of the present invention.

In addition to the above described categories of potential GM modulators, dietary fibre (both soluble and insoluble) have been investigated in this respect. Pea fiber and fructo-oligosaccharides have been found to have some effects on certain GM community members, for example reduced abundance of *Faecalibacterium prausnitzii*. Reduction in *F. prausnitzii* abundance is in stark contrast to the observations made with the present invention.

A purified humic material extracted from a geological sediment of the Leonardite type, has in a study with 15 healthy volunteers been shown to be safe and without any adverse effects when given orally in capsules (Swidsinski et al. 2017). This product seems to have the potential to modulate the human GM, but the results presented in the study were inconsistent, inconclusive and statistically insignificant for the majority of observations. This may be due to the small number of human volunteers in this pilot study and the fact that they were all healthy and presumably not GM-dysbiotic. There were also methodological limitations related to the microbiota-analyses used in this study. For example, the study reports no net increase in the genus *Akkermansia*, while at the same time reporting a statistically significant increase in the abundance of *Akkermansia muciniphila*, the only species of *Akkermansia* known to colonize the human gut.

Beta-glucans are a family of β-D-glucose polysaccharides, widespread in plants and in cell-walls of fungi and bacteria. Other previously described uses of beta-glucan include its use as a drug delivery system that is safe for human use (U.S. Pat. No. 5,032,401A) and as a bulking agent in animal feeds. Oat and other cereal beta-glucans are non-branched mixed beta-1,3/1,4-glucans which are hydrolyzed by enzymes in the gastrointestinal tract and used by microbes as energy substrates. Oat glucans and hydrolysates (oligomers) of oat glucan therefore fall under the definition of prebiotics. By this action cereal beta-glucans, including oat beta-glucan, provide nutrients and may thus support growth of lactobacilli and bifidobacteria.

The human gut does not secrete enzymes that hydrolyze beta-1,3- or beta-1,6-glycosidic linkages and the particulate beta-1,3/1,6-glucan product used as one of the components of the DS. It is therefore resistant to enzymatic digestion in the gastrointestinal tract. It is also a very dense structure which is not readily accessible to microbes in the anaerobic compartments of the intestinal tract, and observations from practical use indicate that the particles are excreted in the feces. The particulate beta-1,3/1,6-glucan components of the DS of the present invention has the technological advantage that it forms a solid gel after autoclaving. It therefore represents an ideal matrix into which other components of DS can be integrated. This is important when formulating DS-products not only for oral administration, but also when used topical in treatment of wound infections or in dental care products.

The basic idea behind the product concept of the present invention is the opposite to that of prebiotics, i.e. the product shall not supply external energy to the GM ecosystem. Instead, in order to prevent and counteract dysbiosis, the purpose of the DS is to force the ecosystem into a mode in which individual species cooperate to share a limited supply of energy. The beta-1,3/1,6-glucan preparation used to illustrate the invention, as shown in the examples, has a different chemical structure from e.g. beta-1,3/1,4-glucans found in oat, and is not utilized as an energy substrate by gut bacteria. It represents a well-characterized beta-glucan in the same chemical category and with the same biological mode of action as soil mushroom beta-glucans, such as for instance lentinan. The beta-1,3/1,6-glucan used in the DS of the present invention acts as a substitute for the mycelial beta-1,3/1,6-glucans found in natural forest soils.

It may be argued that the GM-modulating effect of DS is merely a "fibre-effect" obtained with any humic or lignin structure. In the examples below we have demonstrated that both lignin and pure humic material affect the GM, but their GM-modulating properties differ starkly from that of the DS.

SUMMARY OF THE INVENTION

The deconstructed soil (DS) composition of this invention contains two organic components and one inorganic material found in pristine soils namely:
1) black (oxidized) iron containing humic materials (humics) remaining after microbiological and chemical decay of plant lignocellulose materials in sediments or natural soils,
2) fungal cell-wall beta-1,3/1,6-glucans,
3) inorganic clay material (illite).

The black humic material used in the present study is not a pure humic acid. It contains cellulose/beta-glucans and more than 10% (dry weight basis) of inorganic substances normally present in soils and as such it may be a relevant substitute of a forest soil. We have nevertheless also made DS-formulations enriched with inorganic soil materials, such as clay (illite). We have shown that enrichment with beta-glucans and clay minerals does not change the general microbiota-modulating properties of the basic DS-composition and may therefore be used when there is a need to modify textural properties of DS.

The components of the DS cannot be utilized as energy substrates for microbial growth under anoxic conditions. Nevertheless, the DS has a profound effect on the ecology of anaerobic or micro-aerophilic human GMs, e.g. such as in the colon and cecum. It modulates human GM by strongly favouring the growth of bacterial species associated with good health, disfavoring growth of bacterial groups with putative negative health effects and facilitating recovery of functionally important, rare and vulnerable species. This was highly unexpected since it could not be predicted based on current understanding of how anaerobic microbial ecosystems, such as that of the human gut, are functioning and how individual species in such ecosystems interact.

The DS does not fall under the definitions of a probiotic (live microbes), prebiotic (growth substrates for gut microbes) or a postbiotic (microbial metabolites). The DS of the present invention represents an alternative concept for promoting a healthy GM. We hypothesize that the DS is creating a chemical environment and physical structure for cooperative usage of energy substrates which otherwise are not available for microbes in anaerobic and microaerophilic environments.

The DS composition according to the invention, comprising black humic material and beta-glucans, is formulated for use in modulating anaerobic microbial ecosystems.

DETAILED DESCRIPTION OF THE INVENTION

Soil and Deconstructed Soil (DS)

Natural forest soils consist of a mixture of sandy clay and microbiologically and chemically degraded dead plants, soil-living animals, bacteria and fungi. The surface of soil particles is normally exposed to oxygen and is therefore the habitat of aerobic soil microorganisms. Anaerobic species are restricted to anoxic sediment layers and to the inside of individual soil particles. In anoxic soil environments, the lignin fraction of plant lignocellulose structures cannot be used by microorganisms as a source of energy, and the lignocellulose is very slowly undergoing chemical and microbiological modifications reactions. Dead plants and soil bacteria and fungi will therefore over very long periods of time remain as chemically extremely complex mixtures of humic materials (from plant lignins), polysaccharides (from plant cell-walls) and beta-1,3/1,6-glucans (from fungal cell-walls). Recent plant materials in sediments and soils are turned over fast, while further decay occurs gradually more slowly when the humic materials become more intimately associated with clay minerals. Soils and sediments are therefore "maturing" over very long periods of time and gradually attain the properties like those described in the present invention and which instinctively attract mammals to geophagy.

Iron in sand and clay will, in its trivalent oxidation state (III), bind very strongly to phenolic/quinone groups of humic polymers and form black, insoluble materials, such as in surfaced geological sediments like brown coal and in black forest soils. "Younger" humus-materials produced in anaerobic parts of fresh water lakes, are yellowish or light brown. The black, oxidized humic substances in brown coal sediments and the soluble yellowish/brown humic material formed in anaerobic fresh water environments, are both chemical derivatives of plant lignocellulose fibres once present in green plants. But despite both being derivatives of the same precursors—lignocellulose structures of plants—they differ markedly in their ability to modulate the GM, as shown in the examples below.

Product Need

The product composition designated 'deconstructed soil' (DS), is a sterile substitute for soil as a GM-modulating composition. It is based on natural soil components and its use is to prevent or counteract dysbiosis by applying a novel principle that differs fundamentally from the current market of products aimed at modulating the GM. The current product range of purported GM modulators is commonly divided into three categories:

(1) Probiotics—preparations containing live bacteria or other microbes,
(2) Prebiotics—energy substrates that selectively support growth of putatively beneficial gut bacteria,
(3) postbiotics—metabolites left behind after cultivation of microorganisms.

While these product categories represent large markets, they do not adequately take into account the complex ecology of the GM, a community composed of hundreds of species that form highly complex networks of metabolic interdependencies. For example, introduction of large numbers of one or a few species of probiotic bacteria (mostly lactic acid bacteria) will inevitably change the ecological balance between species in the GM—if the introduced bacteria survive and become new members of the GM. Prebiotic substances (mostly oligosaccharides) are promoted as a means of favouring growth of a limited number of species (putatively beneficial) in the GM, and hence prebiotics will potentially induce changes in the GM ecology. Negative effects of probiotics that are marketed as positive for human and animal health, have been postulated based on theoretical knowledge of GM ecology, but there are also serious warnings based on solid scientific studies. Probiotics may for instance delay normal recovery of human GM after antibiotics treatments, contrary to what is commonly believed and recommended medical practice. Prebiotics—defined as above—also do not comply with the basic ecological principles of the GM, and their efficacy in promoting gut health is questionable.

There is accordingly an unmet demand for products that modulate the GM in accordance with basic laws of microbial ecology in anaerobic environments, such as the DS of the present invention.

Mode of Action

The black humic material component of DS is a polymer of aromatic monomers containing phenolic and quinone moieties which chelate iron (III). This structure may serve as an electron shuttling agent in anaerobic environments. Iron (III) may be reduced to iron (II) in this process, and the quinone moieties reduced to semiquinone and phenolic groups. Reduced iron (II) and phenolic moieties in the humic material polymer may in turn deliver electrons to other microbes in the ecosystem and become re-oxidized. This provides a means by which fermentative microbes can unload excess reducing equivalents, and thus redistribute energy to other community members. Given our current understanding of anaerobic metabolism, this mode of action is insufficient to explain all of our observations, for instance that some strictly anaerobic species are favoured by DS, while others are not. For example, *Bacteroides* spp., a strictly anaerobic group, were among the most prevalent groups in our control experiments, whereas treatment with DS nearly eliminated these species from the assay cultures. This is in distinct contrast to the effects of the purified humic material from fresh water, which showed no effect on these species relative to control. Moreover, the lignin component enhanced growth of putatively harmful *Clostridium perfringens* whereas this species was knocked down by DS. Furthermore, growth of *Prevotella copri* and *Faecalibacterium prausnitzii* were not affected by lignin, whereas the same species were significantly enhanced by DS. More basic research is therefore needed to reveal detailed mechanisms behind the highly unexpected discoveries of the GM-modulating properties of DS.

Potential Applications

The product of this invention should be viewed as a basic formulation that can be used alone or in combination with other products in maintaining an ecologically balanced GM and in addressing conditions related to GM-dysbiosis such as: Obesity, alcoholic and non-alcoholic fatty liver disease, autism, type II diabetes, cardiovascular health, inflammatory bowel disease, irritable bowel syndrome, metabolic syndrome, myalgic encephalomyelitis/chronic fatigue syndrome, ADHD, Parkinson's disease, AIDS, depression, arthritis, allergy. It may also be used as a base formula to support fecal microbiota transplantation (FMT) in the prevention of Clostridium difficile overgrowth. It may also be used as a microbiome modulation adjuvant for cancer drugs, including cancer immune therapy, and cancer vaccines, as well as for vaccines in general. For example, this could be achieved by selectively enhancing the growth of Faecalibacterium and disfavoring growth of Bacteroidaceae, as shown in the examples.

It is implicit in the discoveries described in the examples below that the microbiota modulating ability of the DS has relevance also for other applications than for preventing or treating GM-dysbiosis, for instance to modulate microbiota in wounds and in inflamed periodontal tissues.

It is also implicit that DS may have an application in commercial farming of avians (chicken, turkey) and fish. Commercial chicken production, from fertilized eggs to slaughter, is carried out under technological regimes designed to avoid and prevent microbial exposures chicken have become adapted to during evolution. To make chicken in such environments more robust to incidental exposure to opportunistic pathogens in their production facilities, it may be a good strategy to use a product like DS to beneficially enrich the anaerobic microbial community in their blind-sacks.

Within the aquaculture sector, modern farming of tilapia is of particular relevance for DS use. This tropical fish species is biologically adapted to fresh water ecosystems rich in algae and microbes, and with anaerobic bottom sludges. The fish periodically engulf anaerobic bottom sludge and return to oxygen-rich surface water to graze on phytoplankton. In modern farming in clean water ponds or open net cages, the fish is deprived of such anaerobic inputs, which can be compared to geophagy in mammals. The DS composition of the present invention may therefore be a good substitute.

The deconstructed soil composition according to the invention comprises a beta-1,3/1,6-glucan and a black humic material containing minerals and polysaccharides. The beta-1,3/1,6-glucan added to the black humic material is of fungal type, preferably obtained from yeast. Further the black humic material of the composition comprises iron and oxidized lignate/humic materials. Preferably the black humic material is of the Leonardite type. Optionally the composition of the invention comprises clay minerals.

In a further embodiment of the invention the ratio of beta-1,3/1,6-glucan to black humic material is in the range of 1:100 to 1:1, preferably 5:100, most preferred 3.5:100.

When the deconstructed soil composition of the invention comprises clay minerals the ratio of beta-1,3/1,6-glucan to black humic material to clay minerals is in the range of 1:100:5 to 5:100:15, preferably 3.5:100:10.

The use of the deconstructed soil composition as defined above in the treatment of dysbiosis in vertebrates, particularly mammals, is comprised in another embodiment of the invention. According to other embodiments of the invention said mammal is a human, a pet or a farm animal. Yet other embodiments of the invention encompass the use of the composition wherein said vertebrate is an avian or aquaculture species.

In yet another embodiment of the invention the deconstructed soil composition is used to selectively favour oxygen sensitive and beneficial gut bacteria under anaerobic and microaerophilic conditions. In a further embodiment the deconstructed soil composition is used to selectively disfavour oxygen consuming and detrimental gut bacteria.

In particular embodiments of the invention the deconstructed soil composition is used to enhance the growth of *Faecalibacterium prausnitzii*, *Prevotella copri*, *Akkermansia* mucinophila, *Methanobrevibacter smithii*, Bifidobacteria and *Lactobacillus* species under anaerobic and/or microaerophilic conditions.

In other particular embodiments of the invention the deconstructed soil composition is used to disfavour the growth of *Clostridium perfringens*, *Finegoldia magna*, *Alistipes shahii*, *Staphylococcus*, *Bacteroides* umiformis and/or *Bacteroides vulgatus* under anaerobic and/or microaerophilic conditions.

PRODUCTS, METHODS AND EXPERIMENTS

Test Components

The deconstructed soil of the present invention contains basic components present in forest soils, namely 1) fungal type beta-1,3/1,6-glucan and 2) black humic materials from geological sediments, containing iron and residual polysaccharides, and 3) clay material. For comparisons, the GM modulating properties of 4) pure humic material from fresh water lake and 5) lignin from oat hull was tested.

1) Beta-1,3/1,6-Glucan

Baker's yeast (*Saccharomyces cerevisiae*) was chosen as raw material for making the representative type of soil fungal cell-wall beta-1,3/1,6-glucan, but mycelial fungi may also be used as a source of beta-1,3/1,6-glucans.

The extraction procedure was as follows: A paste of live baker's yeast cells was suspended in distilled water (50 gram/liter) and the suspension stirred for 24 hours at 60° C. to allow the cells to autolyze. Thereafter the insoluble matter, containing mainly crude cell-walls, was collected by centrifugation. To remove soluble matter from the insoluble crude cell-wall sediment, it was subjected to repeated resuspensions in water and sedimentations by centrifugations. This washed cell-wall preparation was suspended in sodium hydroxide for 5 hours at 60-70° C. to detach and partly degrade proteins and lipids from the cell-wall polysaccharides, and the alkali treated cell-wall preparation subjected to repeated cycles of centrifugation and washing in water to remove alkali-solubilized matter. The pH of the washed alkali-treated cell wall slurry was adjusted to 7 with citric acid and the neutralized slurry heated to 80° C. and sieved through a 0.5 mm meshed filter-cloth. The resulting cell-wall paste had a beta-glucan content of 65%, the remaining part being primarily lipids. Preparations containing more than 80% beta-glucan were made by extraction in ethanol.

This extraction procedure is the same as that used in the commercial production of particulate yeast beta-1,3/1,6-glucan products such as NBG (Norwegian Beta Glucan) by the company Biotec Pharmacon ASA or WCBG by the US-based company Biothera Inc.

Ethanol extracted preparations containing 60%, 80% and 98% by weight of beta-1,3/1,6-glucan have all been tested out as suitable carriers for various humic material preparations in the deconstructed soil composition of the present invention. The carrier properties of the different particulate beta-1,3/1,6-glucan preparations have been regarded as good when they swell and form a hydrogel when autoclaved (120 C/20 minutes), also when mixed with humic material preparations and clay. All the beta-1,3/1,6-glucan preparations tested (60%, 80% and 98% betaglucan) had swelling capacities corresponding to at least 100 ml aqueous gel when 5 grams of dry beta-1,3/1,6-glucan was autoclaved in water, also when dry black humic substances, or lignin, was mixed in prior to autoclaving.

The examples 1-30 show the results when using the commercial beta-1,3/1,6-glucan preparation M-Gard (Biotec Pharmacon ASA; www.biotec.no) containing 80% beta-1,3/1,3-glucan. When 5 grams (dry) of this product is suspended in distilled water and autoclaved, it forms a gel volume of 100 ml and any additional water is found in a separate layer. The same gel volume resulted also when M-Gard was mixed with as much as 5 grams of dry black humic materials, and therefore an ideal carrier into which the black humic materials can be intimately integrated.

It should be noted that the amount of beta-1,3/1,6-glucan can be mixed in equal amount with the black humic material, without change of the general pattern of GM-modulating ability.

2) Black Humic Material

The other major component of the deconstructed soil of the present invention was a crude, iron-containing and highly oxidized (black colored) lignate/humic material preparation formed in geological sediments (brown coal) during thousands of years of chemical and microbiological decomposition of organic matter. We considered that product to be representative of microbiologically and chemically modified plant lignins present in black forest soils, differing in chemistry and other properties from native lignin and polysaccharides present in green leaves. The black humic materials used in the experiments shown in the examples 1-30 was a water insoluble, black powder extracted in alkali from brown coal of the Leonardite type from Muster, Germany. It had an ash content of 16% (after burning at 480° C.), consisting mainly of iron (III) oxide.

We have compared the microbiota modulating properties of the DS of the present invention to those of native lignin extracted from oat hulls, and of a pure yellowish (reduced and iron-free) humic material formed in a fresh water lake. We did this to examine if the effects described in the examples, was attributable to a certain degree of "ageing" and "maturation" of humics during microbial and chemical decay. Results from such comparative studies show that the effects of black humic materials differ largely from those of pure humic material from fresh water (Examples 25-27) and native lignin from oat hulls (Examples 28-30).

3) Clay Material

The inorganic component added to the basic DS containing beta-1,3/1,6-glucan and humic material was of the illite-type available in health food stores. It contains aluminium-silicate as the major component.

4) Pure Humic Acid

The pure humic acid used in the experiments presented in examples 25-27 was produced in connection with a research project in limnology at the University of Oslo. Yellow and clear water from an inland lake in the Oslo region was first filtered to remove particulate matters (>1 micron) and then ultra-filtrated (>10 000 D) to concentrate humic substances. After repeated cycles of washing in water and ultra-filtration, the pure humic acid was vacuum dried to a fluffy light-brown powder, with a microfibrillar microscopic structure. This substance was used in the experiments presented in Examples 25-27.

5) Lignin

The lignin used in the experiments shown in Examples 28-30 was extracted from oat hulls as follows: Dry oat hulls (Norgesmøllene AS, Norway) was finely ground to a particle size of 1-2 mm and suspended in water (one weight unit/50 ml), acidified with HCl to pH 1-2 to which 0.5 gram pig pepsin (Arctic Zymes AS, Norway) was added. This mixture underwent pepsin digestion at 37° C. for 24 hours before the solid phase was sedimented and washed with water by repeated centrifugations and sedimentations. The white top layer (cellulose) in the sediment was sucked off and the brown lignin-containing bottom layer washed repeatedly with 96% ethanol to remove any ethanol soluble low molecular substances. The brown powder obtained after air-drying was used in the experiments of Examples 28-30.

Technology for GM Analysis.

It is only relatively recently that scientists have been able to describe the GM at any level of detail. Development of DNA-sequencing technologies has led to an "explosion" of research into the human GM, as well as other complex microbial ecosystems. These efforts have demonstrated the previously unknown complexity and individual nature of the microbial community residing in the gut. The most common approach to surveying the GM is known as marker gene or amplicon DNA sequencing. In the case of bacteria, this entail massively parallel sequencing of a phylogenetic marker gene, usually the gene encoding the small subunit RNA component (16S rRNA) of the ribosome, the cell's protein synthesis machinery.

This gene is found in all bacteria and archaea, and contains parts that are highly conserved as well as variable stretches, making it suitable for phylogenetic comparison. The current gold standard in high-throughput DNA sequencing is the Illumina platform, which has by far the best cost to output ratio. There are a number of different technical approaches as to how samples are prepared for amplicon sequencing on an Illumina apparatus, so called DNA sequencing library preparation. One thing that they all have in common is the amplification of the target DNA fragment by the PCR (polymerase chain reaction) technology. The particulars of this process, as well as downstream treatment of amplified DNA fragments varies substantially according to the protocol used, as do the costs associated with library preparation, as well as the quality of the output data.

We have developed a novel methodology for 16S rRNA gene amplicon sequencing, including a downstream bioinformatics pipeline, for successfully characterizing microbiotas at a large scale (thousands of samples) (de Muinck et al. 2017). Specifically, we have developed a novel library preparation technique that incorporates a third index sequence as part of a second step PCR amplification, reducing the required number of oligo nucleotides necessary for sequencing. The main idea is that dual indices and partial Illumina adapters are added during the first step PCR, while the second reaction uses one generic oligo-nucleotide for all reactions and one custom oligo-nucleotide for every 96 samples (one standard reagent plate), while completing the adapter sequences so that only successfully amplified fragments are sequenced. We have performed extensive benchmarking and optimization of the technique. Since our technology is so flexible, we are able to use it to characterize complex microbial communities from a variety of different sample types. Thus, our method represents a significant advance in amplicon sequencing of bacterial communities in terms of output to cost ratio and is ideally suited to process large sample numbers for production of top-quality data.

Microbiome Assay

The technology described above was used to generate the data shown in the on following examples on how the deconstructed soil (DS) of the present invention, consisting of beta-1,3/1,6-glucan and black humic material, modulates the model human GM microbiota, based on faecal material cultured under either strictly anaerobic or micro-aerophilic conditions. We tested also the effects of the DS to which the clay mineral illite was added. The cultures were grown in 2 ml sterile tubes containing Anaerobe Basal broth (Oxoid), either as controls or with added DS for seven days at 37° C. For anaerobic conditions cultures were grown in airtight jar containing anaerobic GasPak (Thermo) sachets, and an indicator strip for confirming anaerobicity. Microaerophilic cultures were grown in a regular incubator with a loosened cap covering the tubes for the first 24 hours. After 24 hours the caps were tightened. After seven days all cultures were frozen at −80° C. awaiting further processing. Total DNA was extracted from the cultures using the MagAttract PowerSoil DNA kit. The DNA was analysed using the sequencing procedure described above. Sequencing was done to a mean depth of 67,498 (±17,052 s.d.) reads. Sequence reads were classified to the genus level using the Ribosomal Database Project training set (Cole et al. 2014). Further classification to the species level was done by BLAST search (Altschul et al. 1990) against the Genbank 16S rRNA gene sequence archive. If we found a high identity match (>99%) to a single species, this is presented as the taxonomy of a sequence variant. If a sequence was found to have 100% identity with more than one species a sequence variant is presented at the genus level of taxonomy.

SUMMARY OF EXAMPLES

Examples 1-6 demonstrate that under anaerobic conditions deconstructed soil (DS) and deconstructed soil plus illite (DS+) have a positive effect on bacteria linked with positive gut health in a complex gut microbial culture. Further, rare bacterial types are recovered.

Examples 7-12 demonstrate that under anaerobic and microaerophilic conditions DS plus illite (DS+) has a positive effect on bacteria linked with positive gut health in a complex gut microbial culture. Further, rare bacterial types are recovered.

Examples 13-15 demonstrate the specific nature of the invention in that several types of bacteria that are also anaerobic are not favoured by the invention. The examples presented are types that have been linked in a negative way with gut health.

Example 16 demonstrates the specific nature of the invention. The facultatively anaerobic bacterium *Staphylococcus* is not favoured by the invention. *Staphylococcus* is a normal, but minor member of the GM community. Elevated levels of *Staphylococcus* can be an indicator of aerobiosis in the GM.

Examples 17-18 demonstrate the specific nature of the invention in that types of bacteria that are also anaerobic, but not necessarily linked positively or negatively with gut health, are not favoured by the invention.

Examples 19-21 demonstrate the specific nature of the invention in that several types of bacteria that are also anaerobic are not favoured by the invention under microaerophilic conditions. The examples presented are types that have been linked in a negative way with gut health.

Example 22 demonstrates the specific nature of the invention. The facultatively anaerobic bacterium *Staphylococcus* is not favoured by the invention under microaerophilic conditions. *Staphylococcus* is a normal, but minor member of the GM community. Elevated levels of *Staphylococcus* can be an indicator of aerobiosis in the GM.

Examples 23-24 demonstrate the specific nature of the invention in that types of bacteria that are also anaerobic, but not necessarily linked positively or negatively with gut health, are not favoured by the invention under microaerophilic conditions.

Examples 25-27 demonstrate that the effect of pure fresh water humic material on GM under anaerobic conditions, showing that the effects of this humic material differ markedly from that of the DS.

Examples 28-30 demonstrate the effect of oat lignin on GM under anaerobic conditions, showing that the effects of native lignin from cereal food differ markedly from that of the DS.

EXAMPLES

Example 1

Increased relative abundance of Bifidobacterium in an anaerobic human GM microbiota assay system treated with deconstructed soil (DS, n=5) and DS supplemented with Illite (DS+, n=4), compared to untreated controls (C, n=7). The increase in abundance under both treatments is statistically significant relative to controls (p<0.003, Wilcoxon rank sum test). Horizontal lines represent means while dots represent the actual data points.

The results are shown in FIG. 1.

Comment: Several beneficial effects on the human host have been attributed to resident *Bifidobacterium* spp. in the human gut. Further, the abundance of *Bifidobacterium* has been found to be reduced in patients suffering from IBD, obesity, allergies and autism.

Example 2

Increased relative abundance of *Lactobacillus* in an anaerobic human GM microbiota assay system treated with deconstructed soil (DS, n=5), and DS supplemented with Illite (DS+, n=4), compared to untreated controls (C, n=7). The increase in abundance under both treatments is statistically significant relative to controls (p<0.01, Wilcoxon rank sum test). Horizontal lines represent means while dots represent the actual data points.

Figure 2:
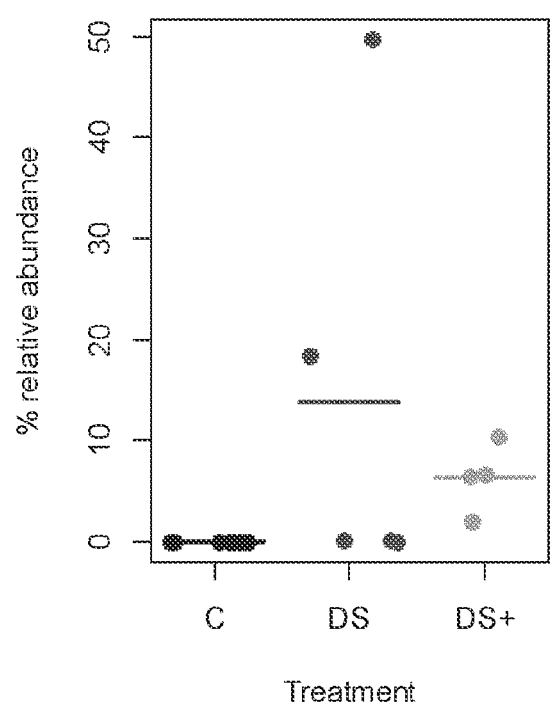

The results are shown in FIG. 2.

Comment: *Lactobacillus* spp., like *L. rhamnosus* or *L. casei*, are widely used in traditional food preservation techniques, and these foods are widely assumed to confer beneficial effects. *Lactobacillus* spp. are also the most widely used probiotic bacterial group.

Example 3

Increased relative abundance of *Prevotella copri* in an anaerobic human GM microbiota assay system treated with deconstructed soil (DS, n=5), and DS supplemented with Illite (DS+, n=4), compared to untreated controls (C, n=7). The increase in abundance under both treatments is statistically significant relative to controls (p<0.01, Wilcoxon rank sum test). Horizontal lines represent means while dots represent the actual data points.

Figure 3:
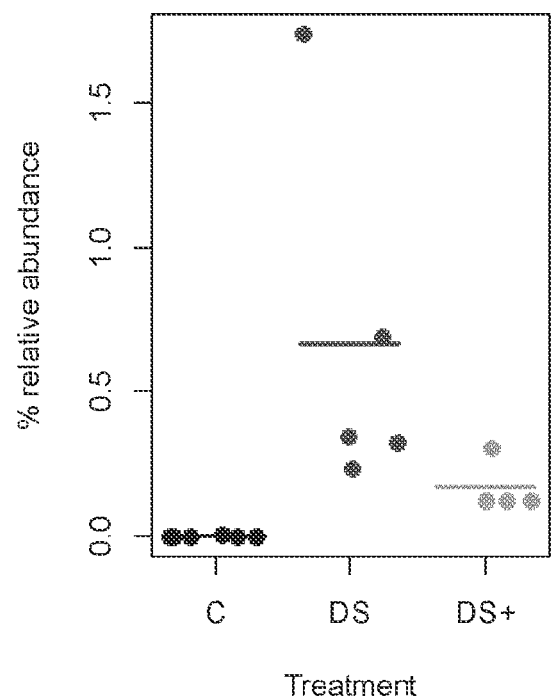

The results are shown in FIG. 3.

Comment: *Prevotella copri* belong to the phylum Bacteroidetes. They can be quite prevalent in the human microbiome, and in particular they have been found at high abundances in hunter-gatherer communities where Western lifestyle diseases are practically absent. Furthermore, reduced abundances of *Prevotella* relative to healthy controls have been found in IBD patients.

Example 4

Increased relative abundance of *Faecalibacterium prausnitzii* in an anaerobic human GM microbiota assay system treated with deconstructed soil (DS, n=5), and DS supplemented with of Illite (DS+, n=4), compared to untreated controls (C, n=7). The increase in abundance under both treatments is statistically significant relative to controls (p<0.004, Wilcoxon rank sum test). Horizontal lines represent means while dots represent the actual data points.

Figure 4:
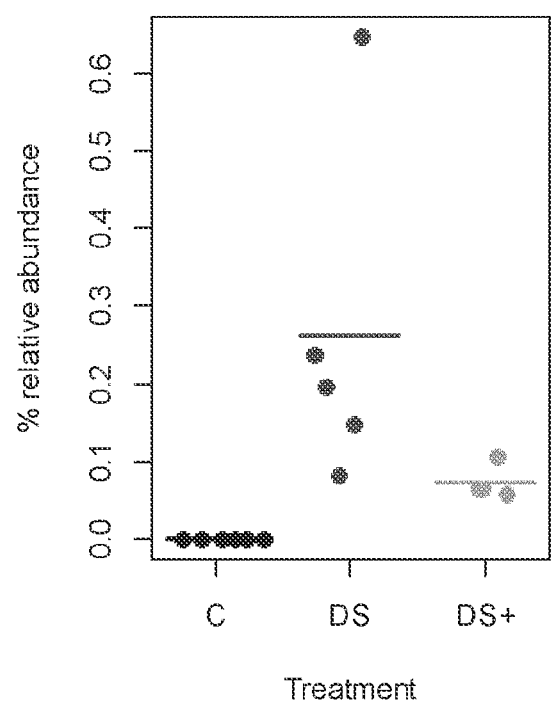

The results are shown in FIG. 4.

Comment *Faecalibacterium prausnitzii* presently contains only the strict anaerobic, butyrate producing and anti-inflammatory species, *Faecalibacterium prausnitzii*. This highly oxygen sensitive and mucus associated bacterium has been found to be depleted in inflammatory bowel disease (IBD). Due to its extreme oxygen sensitivity this bacterium has been very difficult to grow in culture and is therefore a difficult candidate bacterium to be developed as a probiotics.

Example 5

Increased relative abundance of *Methanobrevibacter smithii* in an anaerobic human GM microbiota assay system treated with deconstructed soil (DS, n=5), and DS supplemented with of Illite (DS+, n=4), compared to untreated controls (C, n=7). The increase in abundance under both treatments is statistically significant relative to controls (p<0.02, Wilcoxon rank sum test). Horizontal lines represent means while dots represent the actual data points.

Figure 5:
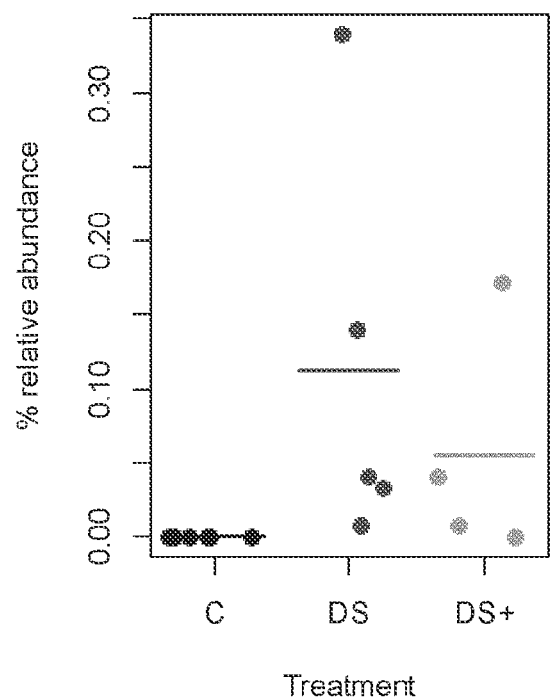

The results are shown in FIG. 5.

Comment *Methanobrevibacter smithii* is an archaeal genus, with *M. smithii* being associated with the human GM. In the human gut it removes hydrogen gas, a common bi-product of bacterial metabolism. This process is strictly anaerobic, and *M. smithii* species is extremely sensitive to oxygen. Depletion of *M. smithii* in the human gut has been proposed as a biomarker for IBD.

Example 6

Increased relative abundance of *Akkermansia muciniphila* in an anaerobic human GM microbiota assay system treated with deconstructed soil (DS, n=5), and DS supplemented with of Illite (DS+, n=4), compared to untreated controls (C, n=7). The increase in abundance under both treatments is statistically significant relative to controls (p<0.02, Wilcoxon rank sum test). Horizontal lines represent means while dots represent the actual data points.

Figure 6:
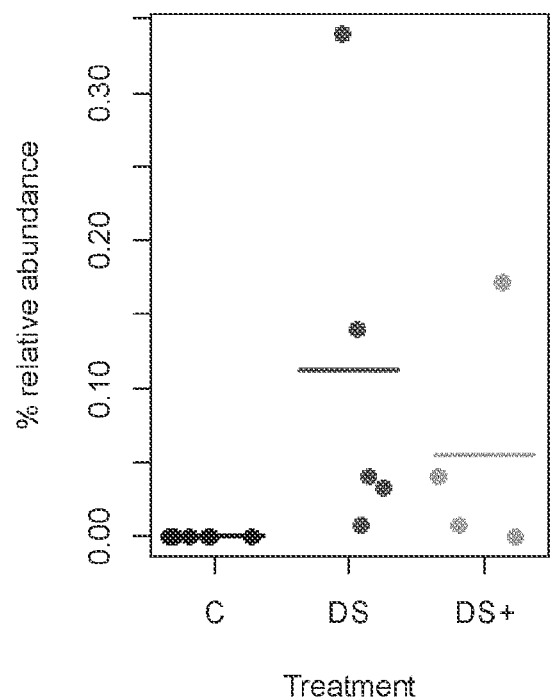

The results are shown in FIG. 6.

Comment *Akkermansia mucinophila* is a genus of strictly anaerobic bacteria belonging to the phylum Verrucomicrobia. They have been shown to be depleted in a mouse model for type 1 diabetes and obesity. *Akkermansia mucinophila* bacteria have been associated with metabolic health in humans and are considered as good candidates for next-generation probiotics.

Example 7

Increased relative abundance of *Bifidobacterium* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The increase in abundance in the MDS+ treated cultures is statistically significant relative to controls (MC) (p<0.05, Wilcoxon rank sum test). Horizontal lines represent means while dots represent the actual data points.

Figure 7:
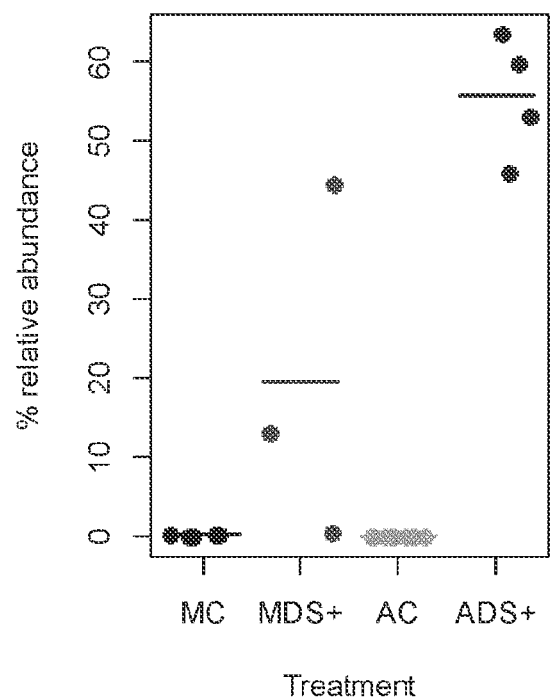

The results are shown in FIG. 7.

Example 8

Increased relative abundance of *Lactobacillus* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). Horizontal lines represent means while dots represent the actual data points.

Figure 8:
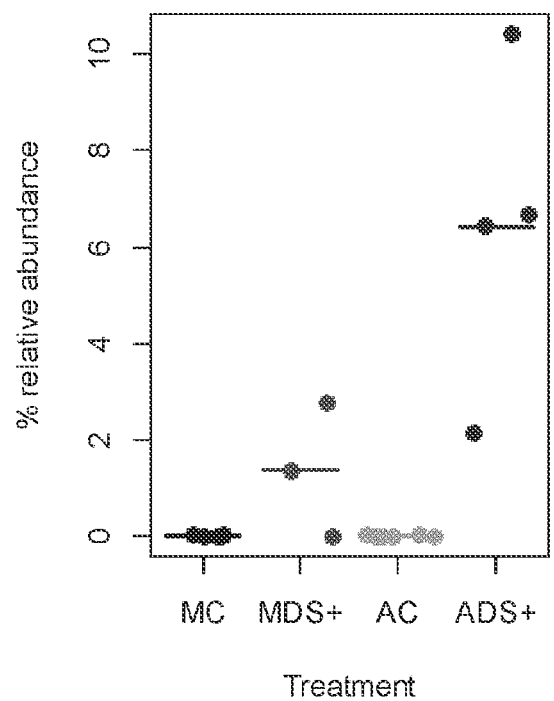

The results are shown in FIG. 8.

Example 9

Increased relative abundance of *Prevotella copri* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The increase in abundance in the MDS+ treated cultures is statistically significant relative to controls (MC) (p<0.05, Wilcoxon rank sum test). Horizontal lines represent means while dots represent the actual data points.

Figure 9:
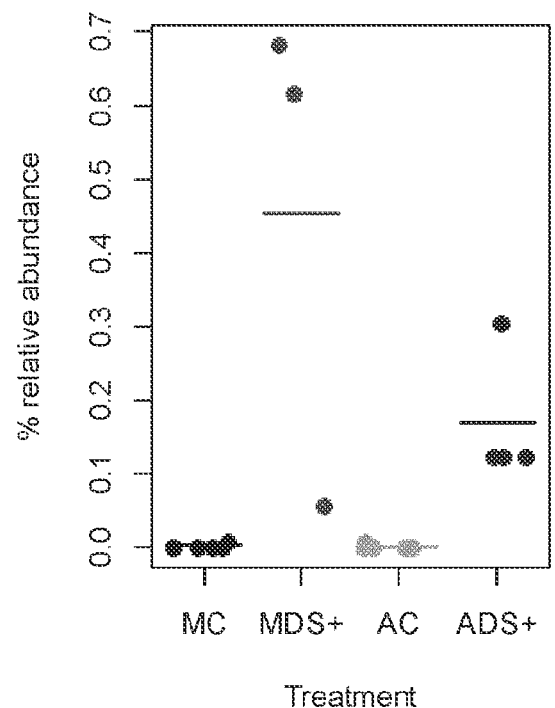

The results are shown in FIG. 9.

Example 10

Increased relative abundance of *Faecalibacterium prausnitzii* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The increase in abundance in the MDS+ treated cultures is statistically significant relative to controls (MC) (p<0.05, Wilcoxon rank sum test). Horizontal lines represent means while dots represent the actual data points.

Figure 10:
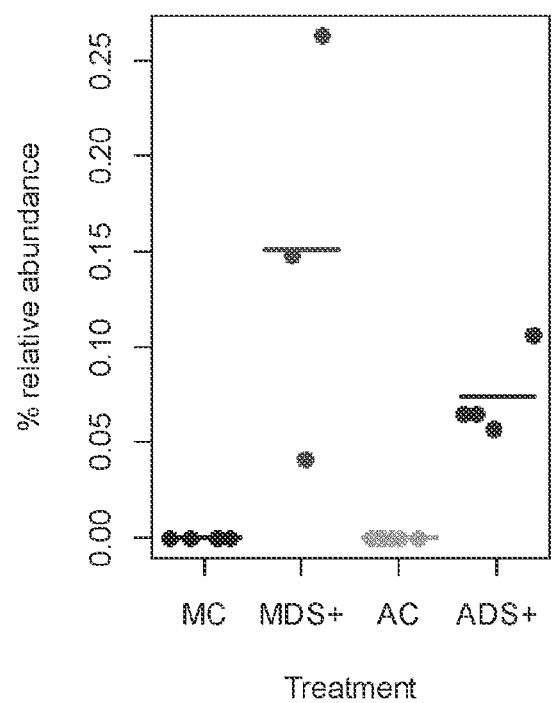

The results are shown in FIG. 10.

Example 11

Increased relative abundance of *Methanobrevibacter smithii* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The increase in abundance in the MDS+ treated cultures is statistically significant relative to controls (MC) (p<0.05, Wilcoxon rank sum test). Horizontal lines represent means while dots represent the actual data points.

Figure 11:
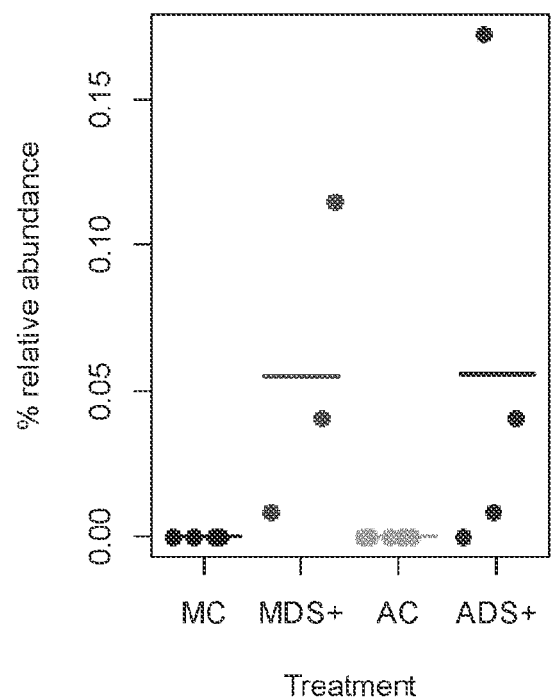

The results are shown in FIG. 11.

Example 12

Increased relative abundance of *Akkermansia mucinophila* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The increase in abundance in the MDS+ treated cultures is statistically significant relative to controls (MC) (p<0.05, Wilcoxon rank sum test). Horizontal lines represent means while dots represent the actual data points.

Figure 12:
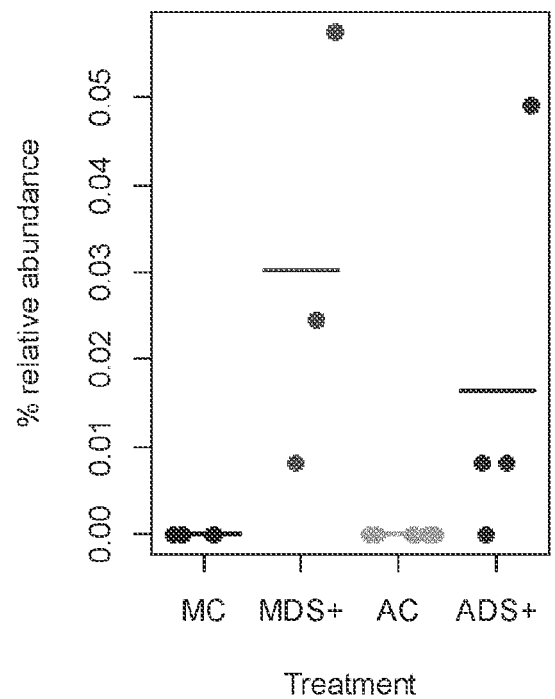

The results are shown in FIG. 12.

Example 13

Decreased relative abundance of *Clostridium perfringens* in an anaerobic human GM microbiota assay system treated with deconstructed soil (DS, n=5) and DS supplemented with Illite (DS+, n=4), compared to untreated controls (C, n=7). The decrease in abundance under both treatments is statistically significant relative to controls (p<0.003, Wilcoxon rank sum test). Horizontal lines represent means while dots represent the actual data points.

Comment *Clostridium perfringens* is widely linked with intestinal diseases in humans and animals.

Figure 13:
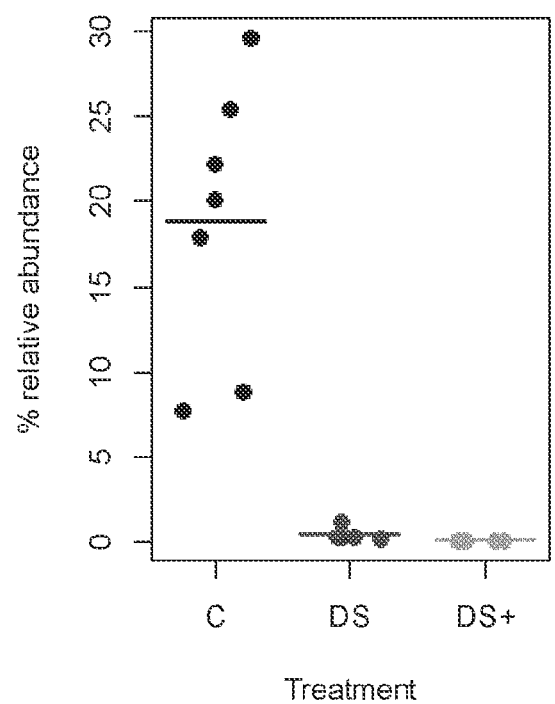

The results are shown in FIG. 13.

Example 14

Decreased relative abundance of *Finegoldia magna* in an anaerobic human GM microbiota assay system treated with deconstructed soil (DS, n=5) and DS supplemented with Illite (DS+, n=4), compared to untreated controls (C, n=7). The decrease in abundance under both treatments is statistically significant relative 5 to controls (p<0.05, Wilcoxon rank sum test). Horizontal lines represent means while dots Comment *Finegoldia magna* acts as an opportunistic human pathogen.

Figure 14:
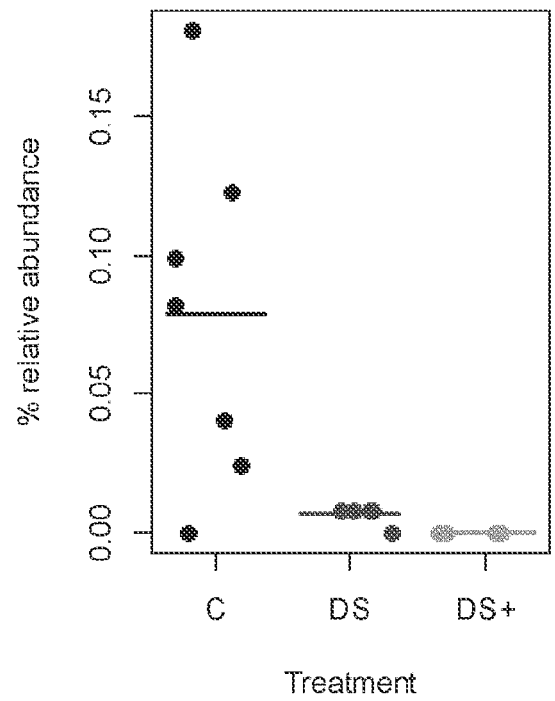

The results are shown in FIG. 14

Example 15

Decreased relative abundance of *Alistipes shahii* in an anaerobic human GM microbiota assay system treated with deconstructed soil (DS, n=5) and DS supplemented with Illite (DS+, n=4), compared to untreated controls (C, n=7). The decrease in abundance under both treatments is statistically significant relative to controls (p<0.01, Wilcoxon rank sum test). Horizontal lines represent means while dots represent the actual data points.

Comment Increased levels of *Alistipes* spp. have been associated with increased pain in children with irritable bowel syndrome.

Figure 15:
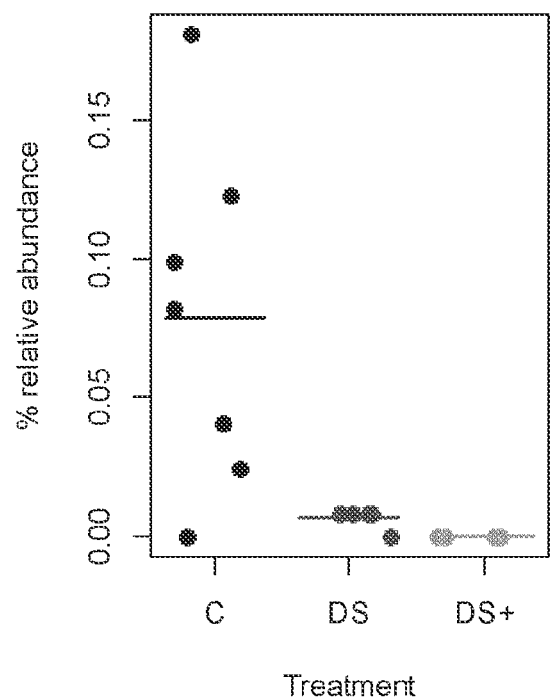

The results are shown in FIG. 15.

Example 16

Decreased relative abundance of *Staphylococcus* in an anaerobic human GM microbiota assay system treated with deconstructed soil (DS, n=5) and DS supplemented with Illite (DS+, n=4), compared to untreated controls (C, n=7). Horizontal lines represent means while dots represent the actual data points.

Comment *Staphylococcus* is a facultative anaerobe and a normal, but minor member of the GM community. Elevated levels of *Staphylococcus* can be an indicator of aerobiosis in the GM.

Figure 16:
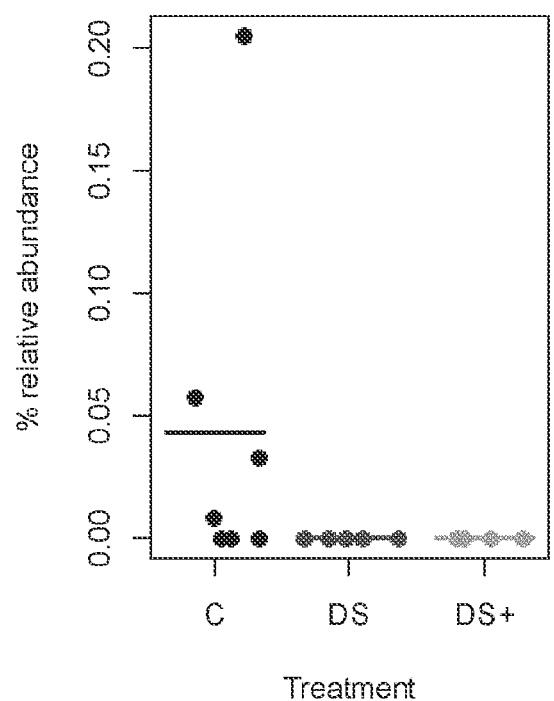

The results are shown in FIG. 16.

Example 17

Decreased relative abundance of *Bacteroides uniformis* in an anaerobic human GM microbiota assay system treated with deconstructed soil (DS, n=5) and DS supplemented with Illite (DS+, n=4), compared to untreated controls (C, n=7). The decrease in abundance under both treatments is statistically significant relative to controls (p<0.006, Wilcoxon rank sum test). Horizontal lines represent means while dots represent the actual data points.

Figure 17:
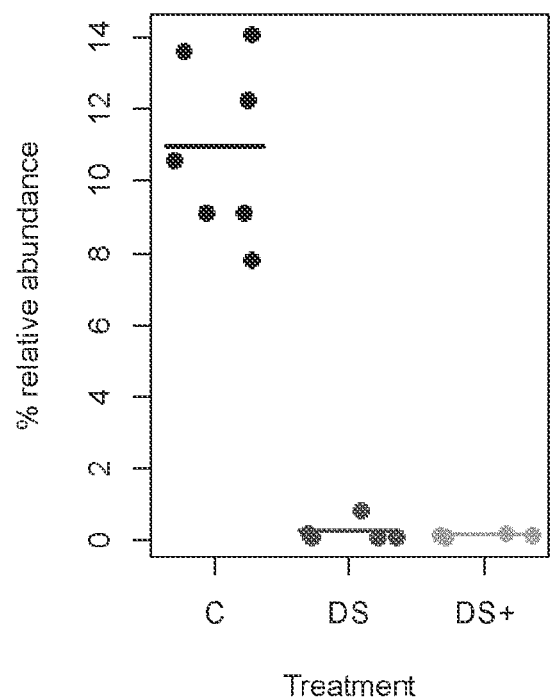

The results are shown in FIG. 17.

Example 18

Decreased relative abundance of *Bacteroides vulgatus* in an anaerobic human GM microbiota assay system treated with deconstructed soil (DS, n=5) and DS supplemented with Illite (DS+, n=4), compared to untreated controls (C, n=7). The decrease in abundance under both treatments is statistically significant relative to controls (p<0.006, Wilcoxon rank sum test). Horizontal lines represent means while dots represent the actual data points.

Figure 18:
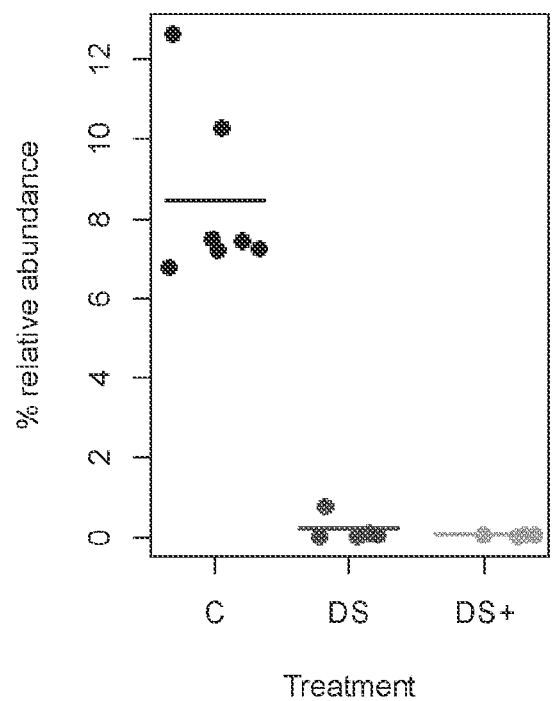

The results are shown in FIG. 18.

Example 19

Decreased relative abundance of *Clostridium perfringens* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The decrease in abundance in the MDS+ treated cultures is statistically significant relative to controls (MC) (p<0.05, Wilcoxon rank sum test). Horizontal lines represent means while dots represent the actual data points.

Figure 19:
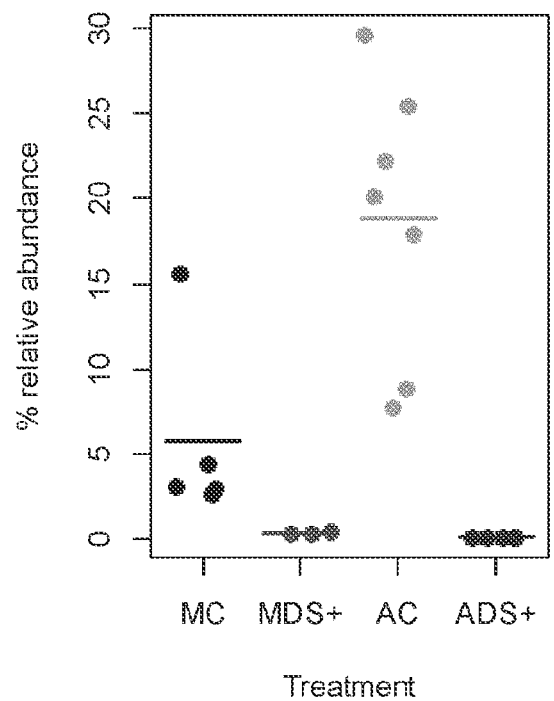

The results are shown in FIG. 19.

Example 20

Decreased relative abundance of *Finegoldia magna* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The decrease in abundance in the MDS+ treated cultures is statistically significant relative to controls (MC) (p<0.05, Wilcoxon rank sum test). Horizontal lines represent means while dots represent the actual data points.

Figure 20:
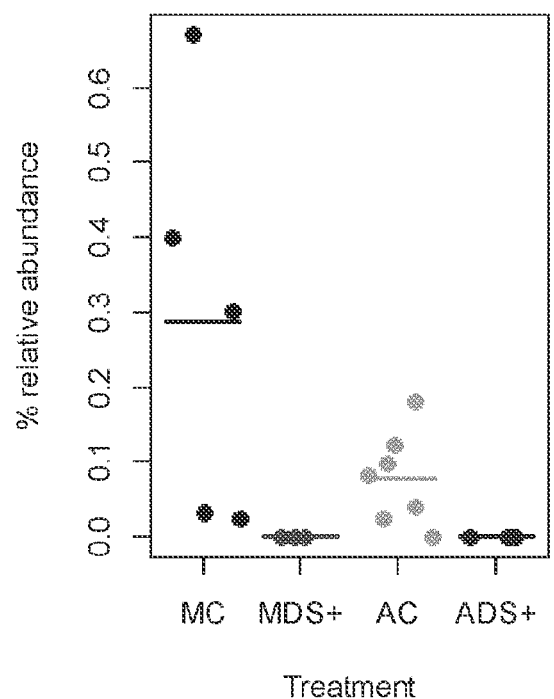

The results are shown in FIG. 20.

Example 21

Decreased relative abundance of *Alistipes shahii* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The decrease in abundance in the MDS+ treated cultures is statistically significant relative to controls (MC) (p<0.04, Wilcoxon rank sum test). Horizontal lines represent means while dots represent the actual data points.

Figure 21:
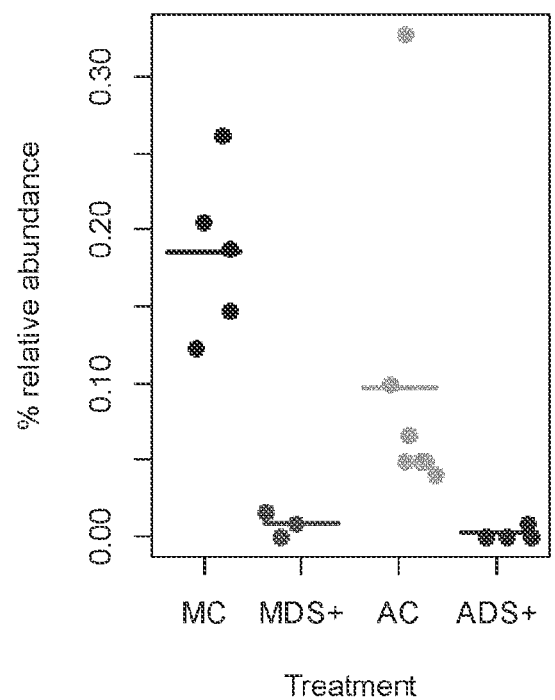

The results are shown in FIG. 21.

Example 22

Decreased relative abundance of *Staphylococcus* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). Horizontal lines represent means while dots represent the actual data points.

Figure 22:
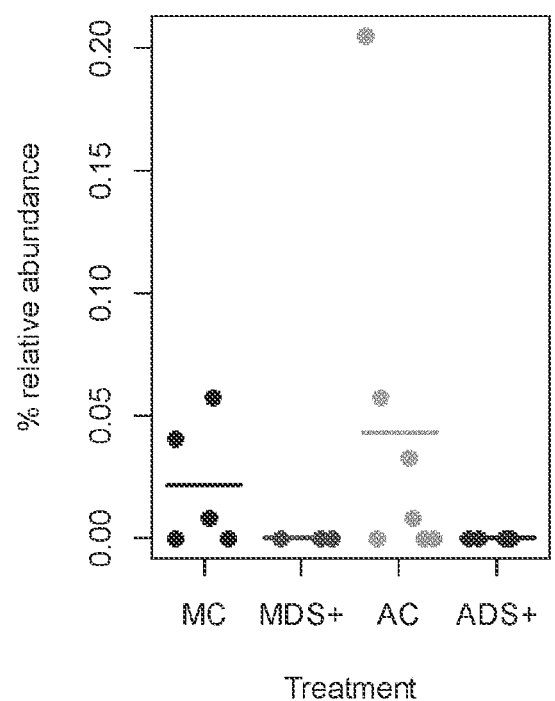

The results are shown in FIG. 22.

Example 23

Decreased relative abundance of *Bacteroides uniformis* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The decrease in abundance in the MDS+ treated cultures is statistically significant relative to controls (MC) (p<0.04, Wilcoxon rank sum test). Horizontal lines represent means while dots represent the actual data points.

Figure 23:
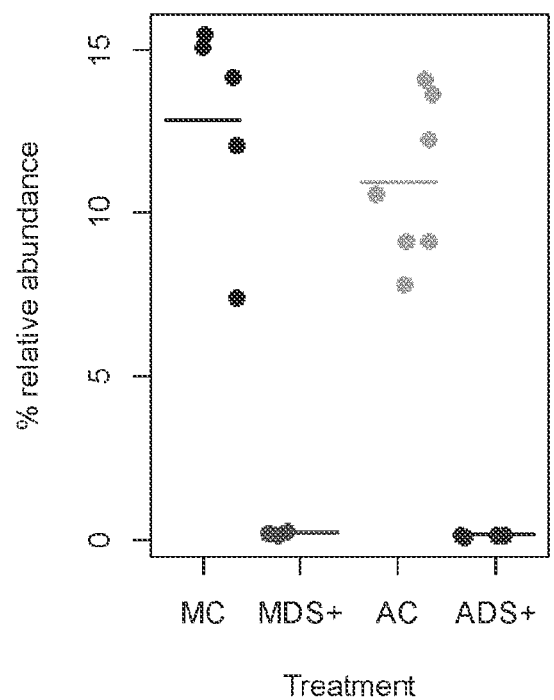

The results are shown in FIG. 23.

Example 24

Decreased relative abundance of *Bacteroides vulgatus* in a microaerophilic human GM microbiota assay system treated with deconstructed soil supplemented with Illite (MDS+, n=3), compared to untreated controls (MC, n=5). The corresponding anaerobic assay is included for comparison (AC=controls, ADS+=DS supplemented with Illite). The decrease in abundance in the MDS+ treated cultures is statistically significant relative to controls (MC) (p<0.04, Wilcoxon rank sum test). Horizontal lines represent means while dots represent the actual data points.

Figure 24:
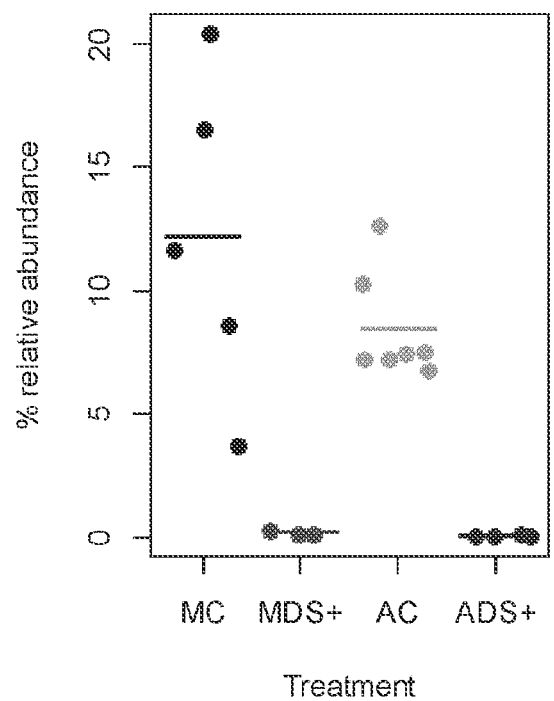

The results are shown in FIG. 24.

Example 25

Increased relative abundance of *Bifidobacterium* in an anaerobic human GM microbiota assay system treated with deconstructed soil (DS, n=5) and DS supplemented with Illite (DS+, n=4), compared to untreated controls (C, n=7) and a pure humic material from fresh water (PHA, n=4). While the mean relative abundance under the PHA treatment is significantly than controls (p=0.04, Wilcoxon rank sum test), the effect of PHA is clearly reduced relative to DS and DS+. Horizontal lines represent means while dots represent the actual data points.

Figure 25:
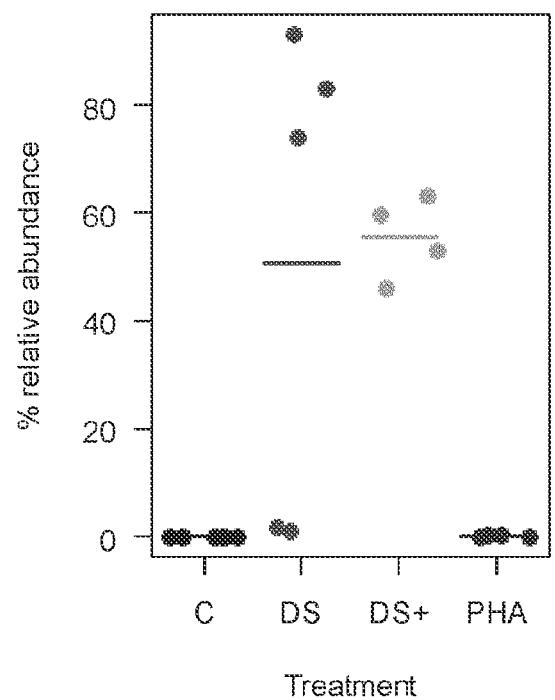

The results are shown in FIG. 25.

Example 26

Decreased relative abundance of *Bacteroides uniformis* in an anaerobic human GM microbiota assay system treated with deconstructed soil (DS, n=5) and DS supplemented with Illite (DS+, n=4), compared to untreated controls (C, n=7) and a pure humic material from fresh water (PHA, n=4). The PHA treatment is not significantly different from the controls, as opposed to DS and DS+. Horizontal lines represent means while dots represent the actual data points.

Figure 26:
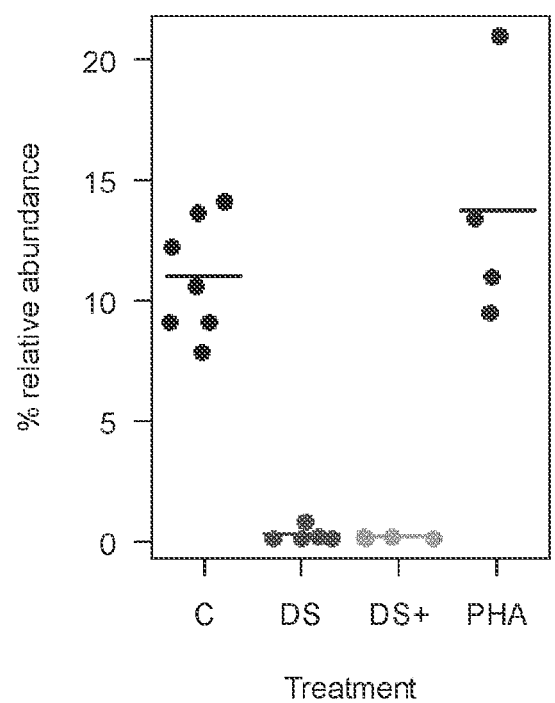

The results are shown in FIG. 26.

Example 27

Decreased relative abundance of *Bacteroides vulgatus* in an anaerobic human GM microbiota assay system treated with deconstructed soil (DS, n=5) and DS supplemented with Illite (DS+, n=4), compared to untreated controls (C, n=7) and a pure humic material from fresh water (PHA, n=4). Relative abundance is significantly elevated in the PHA treatment relative to controls (p=0.02, Wilcoxon rank sum test), while DS and DS+ had the opposite effect. Horizontal lines represent means while dots represent the actual data points.

Figure 27:
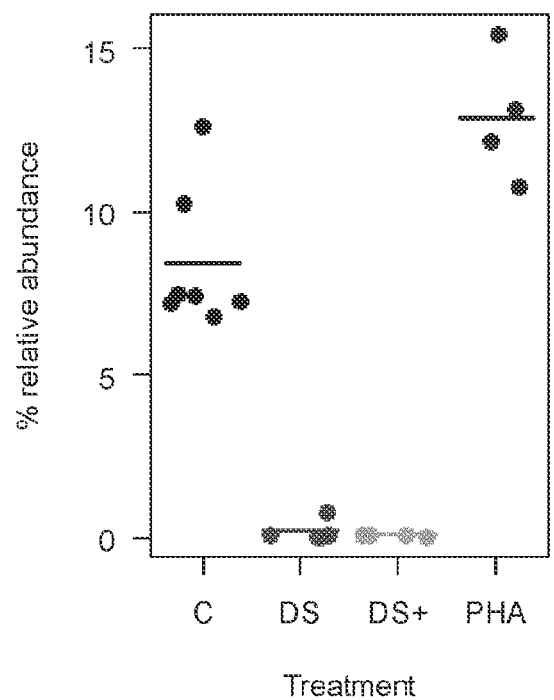

The results are shown in FIG. 27.

Example 28

Decreased relative abundance of *Clostridium perfringens* in an anaerobic human GM microbiota assay system treated with deconstructed soil (DS, n=5) and DS supplemented with Illite (DS+, n=4), compared to untreated controls (C, n=7) and lignin (Lig, n=5). Relative abundance is significantly elevated in the lignin treatment relative to controls (p<0.01, Wilcoxon rank sum test), while DS and DS+ had the opposite effect. Horizontal lines represent means while dots represent the actual data points.

Figure 28:
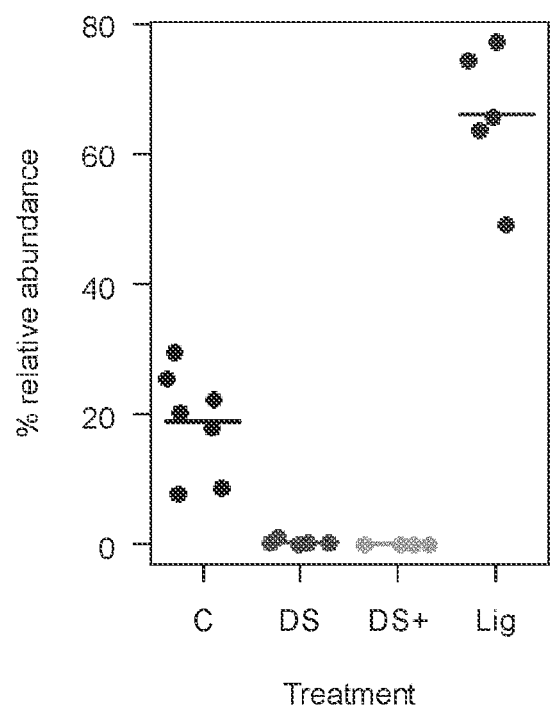

The results are shown in FIG. 28.

Example 29

Increased relative abundance of *Prevotella copri* in an anaerobic human GM microbiota assay system treated with deconstructed soil (DS, n=5) and DS supplemented with Illite (DS+, n=4), compared to untreated controls (C, n=7) and lignin (Lig, n=5). The lignin treatment did not differ significantly from the controls, while relative abundances were elevated in the DS and DS+ treatments. Horizontal lines represent means while dots represent the actual data points.

Figure 29:
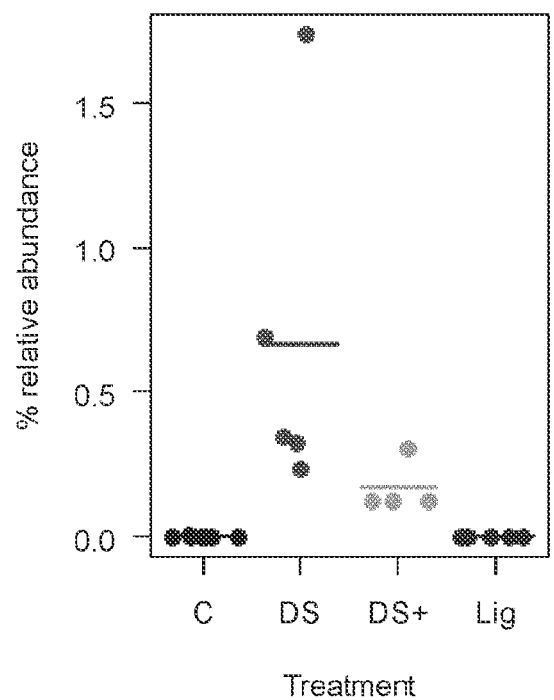

The results are shown in FIG. 29.

Example 30

Increased relative abundance of *Faecalibacterium prausnitzii* in an anaerobic human GM microbiota assay system treated with deconstructed soil (DS, n=5) and DS supplemented with Illite (DS+, n=4), compared to untreated controls (C, n=7) and lignin (Lig, n=5). The lignin treatment did not differ significantly from the controls, while relative abundances were elevated in the DS and DS+ treatments. Horizontal lines represent means while dots represent the actual data points.

Figure 30:
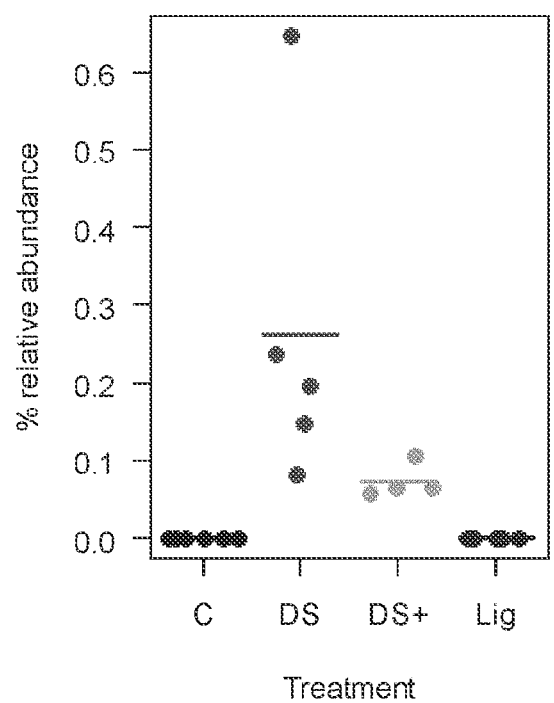

The results are shown in FIG. 30.

The invention claimed is:

1. A deconstructed soil composition comprising a black humic material and a beta-glucan, wherein the beta-glucan is a beta-1,3/1,6-glucan purified from a fungus that is recalcitrant to microbial degradation, and wherein the black humic material comprises iron and lignocellulose.

2. The composition according to claim 1, wherein the beta-glucan is a beta-1, 3/1, 6-glucan extracted and purified from yeast.

3. The composition according to claim 1, wherein the black humic material is of a Leonardite material.

4. The composition according to claim 1, wherein the composition further comprises clay minerals.

5. The composition according to claim 1, wherein the ratio of beta-1, 3/1, 6-glucan to black humic material is in the range of 1:100 to 1:1 by dry weight.

6. The composition according to claim 5, wherein the ratio of beta-1, 3/1,6-glucan to black humic material is 3.5:100 by dry weight.

7. The composition according to claim 4, wherein the ratio of beta-1, 3/1, 6-glucan to black humic material to clay minerals is in the range of 1:100:5 to 5:100:15 by dry weight.

8. The composition according to claim 7, wherein the ratio of beta-1, 3/1,6-glucan to black humic material to clay minerals is 3.5:100:10 by dry weight.

9. A method of modulating anaerobic microbial ecosystems in a target organism, wherein the target organism is selected from the group consisting of mammals, and avian species, comprising applying the composition according to claim 1 to the ecosystem.

10. A method of treating and/or reducing a risk of gut microbiota dysbiosis by modulating anaerobic microbial ecosystems in a target organism, comprising administering the composition of claim 1 to the target organism, wherein the target organism is selected from the group consisting of mammals, avian species, and aquaculture species.

11. The method of claim 10, wherein the mammal is a human.

12. The method of claim 9, wherein the mammal is a pet or a farm animal.

13. The method of claim 10, wherein oxygen sensitive and beneficial gut bacteria are selectively favoured under anaerobic and microaerophilic conditions.

14. The method of claim 10, wherein oxygen sensitive and detrimental gut bacteria are selectively disfavoured under anaerobic and microaerophilic conditions.

15. The method of claim 10, wherein the growth of *Faecalibacterium prausnitzii* or *Prevotella copri* or *Akkermansia mucinophila* or *Methanobrevibacter smithii* or *Bifidobacteria* or *Lactobacillus* or *Faecalibacterium prausnitzii* or *Lactobacillus* is enhanced under anaerobic and microaerophilic conditions.

16. The method of claim 10, wherein the growth of *Clostridium perfringens* or *Finegoldia magna* or *Alistipes shahii* or *Staphylococcus* or *Bacteroides umiformis* or *Bacteroides vulgatus* is disfavoured under anaerobic and microaerophilic conditions.

* * * * *